(12) United States Patent
Chao et al.

(10) Patent No.: US 8,142,484 B2
(45) Date of Patent: Mar. 27, 2012

(54) VERTEBRAL FIXATION PLATE ASSEMBLY

(75) Inventors: Ching-Kong Chao, Danshuei Township, Taipei County (TW); Wen-Hsien Hsu, Taishan Township, Taipei County (TW); Ching-Chi Hsu, Jhudong Township, Hsinchu County (TW); Hsi-Ching Hsu, Jhongli (TW); Yu-Hsiang Tsai, Taipei (TW)

(73) Assignee: National Taiwan University of Science and Technology, Taipei (TW)

( * ) Notice: Subject to any disclaimer, the term of this patent is extended or adjusted under 35 U.S.C. 154(b) by 885 days.

(21) Appl. No.: 12/190,981

(22) Filed: Aug. 13, 2008

(65) Prior Publication Data

US 2009/0210009 A1 Aug. 20, 2009

(30) Foreign Application Priority Data

Jan. 17, 2008 (TW) .............................. 97201046 U

(51) Int. Cl.
*A61B 17/80* (2006.01)
(52) U.S. Cl. ...................................................... 606/280
(58) Field of Classification Search .................. 606/70, 606/71, 246, 280; 623/17.11, 17.16
See application file for complete search history.

(56) References Cited

U.S. PATENT DOCUMENTS

| 5,735,853 | A | * | 4/1998 | Olerud ............................. 606/71 |
| 6,156,037 | A | * | 12/2000 | LeHuec et al. ................. 606/247 |
| 2005/0177161 | A1 | * | 8/2005 | Baynham et al. ............... 606/69 |
| 2007/0093838 | A1 | * | 4/2007 | Khodadadyan-Klostermann et al. .............................. 606/70 |

\* cited by examiner

*Primary Examiner* — Nicholas Woodall
(74) *Attorney, Agent, or Firm* — Guice Patents PLLC

(57) ABSTRACT

A vertebral fixation plate assembly for insertion into the resection site between two vertebrae of a patients vertebral column and fixation to front or lateral side of the two adjacent vertebral bodies above and below the resection site by means of surgical implantation is disclosed to include a fixation plate that has a plurality of round holes and elongated holes and an opening on the middle, a plurality of bone screws respectively inserted through the round holes and elongated holes for fastening the fixation plate to the patient's vertebral column, and a cage affixed to the opening on the fixation plate and holding holes cut through the periphery for bone fusion and grow. The cage is linked to a vertebral spacer for artificial vertebrae by means of bone fusion to prevent vertebral sinking or slipping of the vertebral spacer and to improve bone fusion efficiency.

18 Claims, 5 Drawing Sheets

VERTEBRAL FIXATION PLATE ASSEMBLY

BACKGROUND OF THE INVENTION

1. Field of the Invention

The present invention relates to vertebral reconstruction and vertebral body replacement and more particularly, to a vertebral fixation plate assembly for fixation of thoracic or lumber vertebrae that improves bone fusion efficiency.

2. Description of the Related Art

Vertebral reconstruction and vertebral body replacement commonly uses a vertebral spacer to treat (substitute for) vertebrae destruction or vertebral body damaged by tumor. By means of surgical operation to remove disease vertebral body, a vertebral spacer is inserted into the resection site, and then a fixation device is affixed to the front or lateral side of the vertebral column with pedicle screws to enhance the stability, enabling the vertebral column to resume its function, reducing the patient's pain, and assisting recovery.

Regular fixation devices for this purpose include two types, the fixation plate and the fixation rod. However, these two different types of fixation devices are still not satisfactory in function in clinical practice due to the drawbacks: (1) A fixation plate type fixation device wears quickly with use and may be loosed from the bone screws due to thin and weak border edge around each mounting hole, affecting fixation stability and bone fusion progress; (2) A fixation rod type fixation device requires installation of two sets of transverse links to achieve the desired strength and stiffness, complicating the implantation procedure. Further, conventional fixation devices have no means for carrying autograft bone, bone allograft or biomedical bone substitute to facilitate bone fusion.

Therefore, it is desirable to provide a vertebral fixation device that eliminates the aforesaid drawbacks.

SUMMARY OF THE INVENTION

The present invention has been accomplished under the circumstances in view. It is therefore the main object of the present invention to provide a vertebral fixation plate assembly, which is designed for insertion into the resection site between two vertebrae of a patient where a vertebral spacer is implanted and fixation to front or lateral side of the vertebra bodies above and below the resection site to reinforce the stability of the patient's vertebral column. It is another object of the present invention to provide a vertebral fixation plate assembly, which is provided with a bone fusion cage for connection with the vertebral spacer to prevent vertebral sinking or slipping of the vertebral spacer to improve bone fusion efficiency.

To achieve these and other objects and according to one embodiment of the present invention, a vertebral fixation plate assembly is provided for insertion into the resection site between two vertebrae of a patient's vertebral column and fixation to front or lateral side of the two vertebral bodies above and below the resection site. The vertebral fixation plate assembly comprises a fixation plate, which has an opening on a middle part and extending to one side and a plurality of holes at the two distal ends, a plurality of bone screws inserted through the holes of the fixation plate for fastening the fixation plate to a patient's vertebral column, and a cage, which has a cage body mounted in the opening of the fixation plate and a plurality of fusion holes cut through the periphery of the cage body for bone fusion and growth.

To achieve these and other objects and according to another embodiment of the present invention, a vertebral fixation plate assembly is provided for insertion into the resection site between two vertebrae of a patient's vertebral column and fixation to front or lateral side of the two adjacent vertebral bodies above and below the resection site. The vertebral fixation plate assembly comprises a fixation plate, which has an opening on a middle part and extending to one side and a plurality of holes at the two distal ends, a plurality of bone screws inserted through the holes of the fixation plate for fastening the fixation plate to a patient's vertebral column, a cage, which has a cage body mounted in the opening of the fixation plate and a plurality of fusion holes cut through the periphery of the cage body for bone fusion and growth, and a link connected between two bone screws at two sides of the opening of the fixation plate to hold down the cage.

DETAILED DESCRIPTION OF THE PREFERRED EMBODIMENT

Referring to FIGS. 1-5, a vertebral fixation plate assembly in accordance with the present invention is for use in a patient whose thoracic or lumbar vertebrae lose the support function. The vertebral fixation plate assembly is inserted into a resection site between two vertebrae of a patient's vertebral and then affixed to the front or lateral side of the two adjacent vertebral bodies above and below the resection site during a surgical operation, enabling the vertebral column to support the patient's body. The vertebral fixation plate assembly is comprised of a fixation plate 1, a plurality of bone screws 2, a cage 3, and a link 4.

Figure 2:
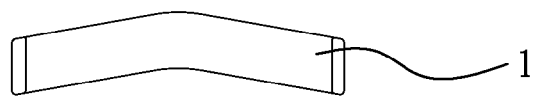
FIG. 2 is a top view of the fixation plate according to the present invention.

The fixation plate 1 can be a metal plate made of, for example, titanium. Following fast development of biomedical material technology, many biomedical materials have been proved suitable for making the fixation plate. For example, PEEK (polyetheretherketone) may be used. As shown in FIG. 2, the fixation plate 1 has a symmetrically arched cross section so that each of the two sloping top walls of the ridge roof thereof defines with the horizontal reference line at the ridge a contained angle θ within 40°. When the bone screws 2 are fastened to the vertebrae, the left-sided bone screws and the right-sided bone screws define a contained angleθ within 40° (see FIG. 5), enhancing the engagement force of the bone screws 2 and increasing the pullout strength. Therefore, the fixation plate 1 fits any of a variety of vertebral sizes and correction requirements.

Figure 1:
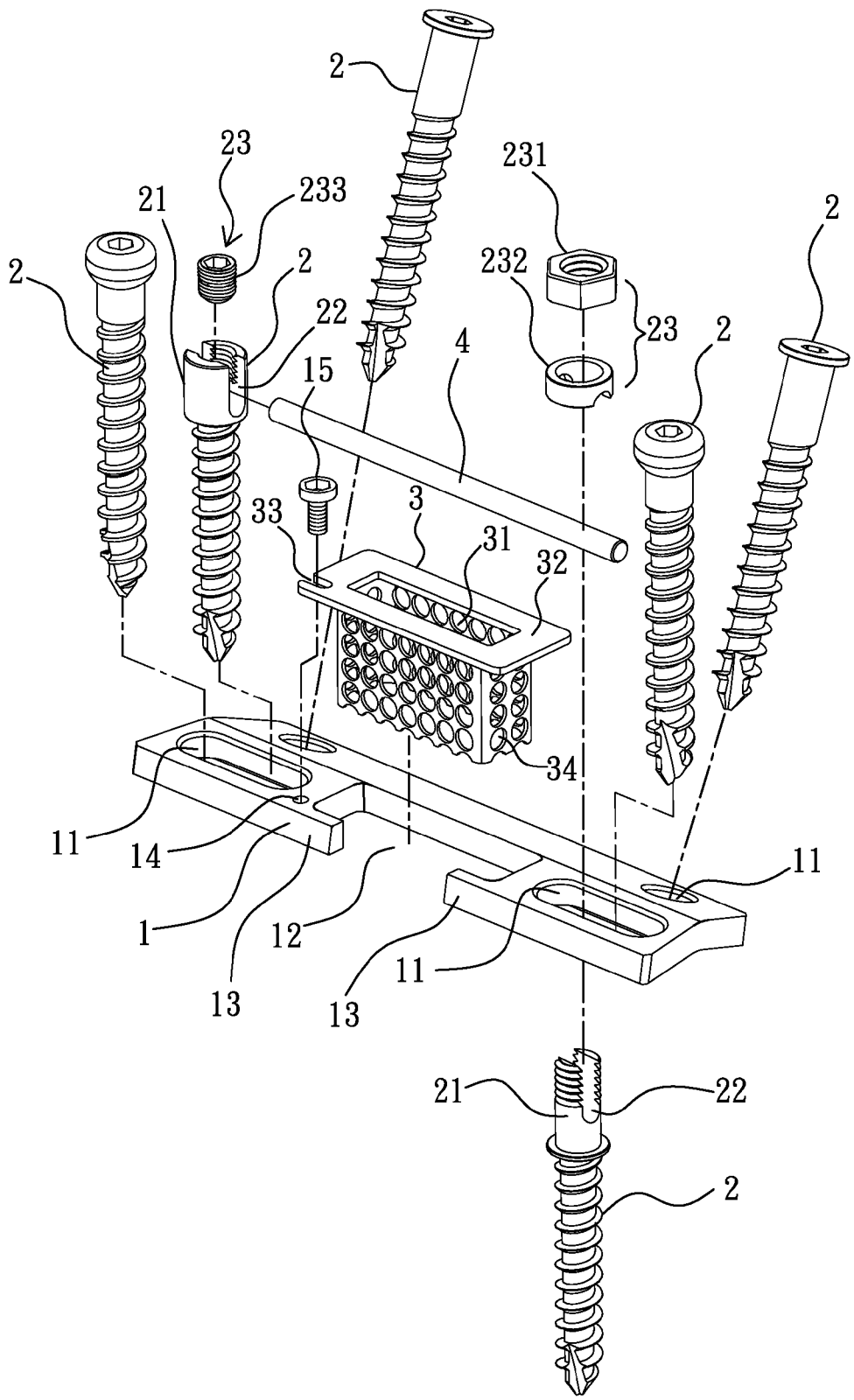
FIG. 1 is an exploded view of a vertebral fixation plate assembly in accordance with the present invention.
Figure 3:
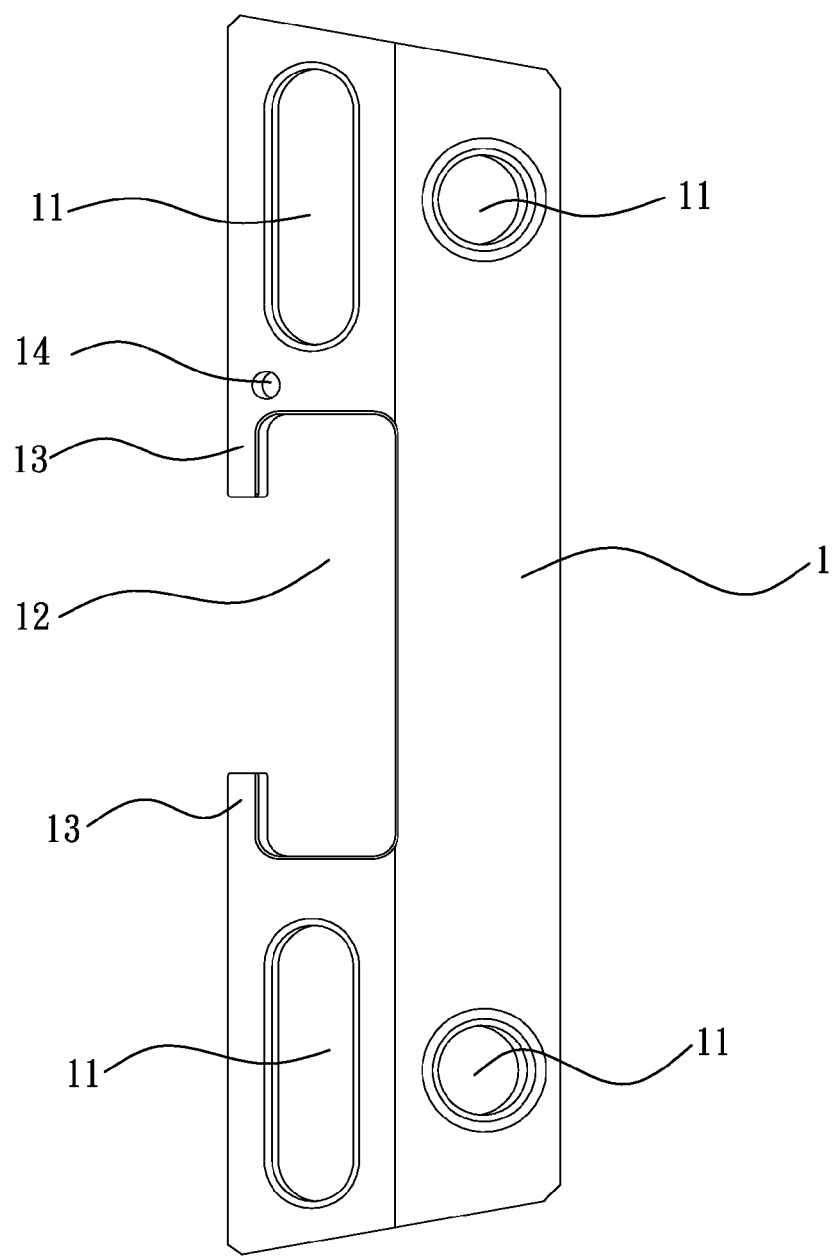
FIG. 3 is a left side of the fixation plate according to the present invention.

The fixation plate 1 has a plurality of holes 11 cut through the top and bottom sides in the four corners for the passing of the bone screws 2 so that the bone screws 2 can affix the fixation plate 1 to a vertebral column. The holes 11 that are located on the left side are elongated holes. The holes 11 that are located on the right side are circuit holes. As shown in FIGS. 1 and 3, the fixation plate 1 further has an opening 12 on the middle of the left side between the two elongated holes 11, two protrusions 13 suspending in the outer open side of the opening 12 and aimed at each other for stopping the cage 3 in the opening 12, and a mounting screw hole 14 on one protrusion 13 for the mounting of a tie screw 15 through the hole 33 of the cage 3 to affix the cage 3 to the fixation plate 1.

The bone screws 2 are respectively inserted through the holes 11 to affix the fixation plate 1 to two adjacent vertebrae of the patient's vertebral column, enhancing the stability of the vertebral column. Each of the two bone screws 2 that are to be mounted in the left-sided elongated holes 11 and disposed close to the opening 12 has a modified head 21 for securing the link 4. As shown in FIG. 1, the head 21 has a longitudinal crevice 22 for receiving one end of the link 4. After insertion of one end of the link 4 into the longitudinal crevice 22, a holding down device 23 is fastened to the head 21 to hold down the link 4, prohibiting the link 4 from falling out of the bone screw 2 and enabling the link 4 to hold down the cage 3. The holding down device 23 may be variously embodied. FIG. 1 illustrates two different forms. According to the form shown on the right side in FIG. 1, the holding down device 23 is comprised of a locating ring 232 and a nut 231. The locating ring 232 is sleeved onto the head 21 and attached to the link 4. The nut 231 is threaded onto the threads on the periphery of the head 21 to force the locating ring 232 downwards against the link 4.

According to the form shown on the left side in FIG. 1, the head 21 of the corresponding bone screw 2 is shaped like a barrel and internally threaded, and the holding down device 23 is a holding down screw 233. After insertion of one end of the link 4 into the longitudinal crevice 22 of the internally threaded barrel-like head 21, the holding down screw 233 is threaded into the internally threaded barrel-like head 21 and stopped against the link 4 to hold down the link 4 in place. It is to be understood that the longitudinal crevice 22 is threaded and configured subject to the configuration of the holding down screw 233.

Figure 4:
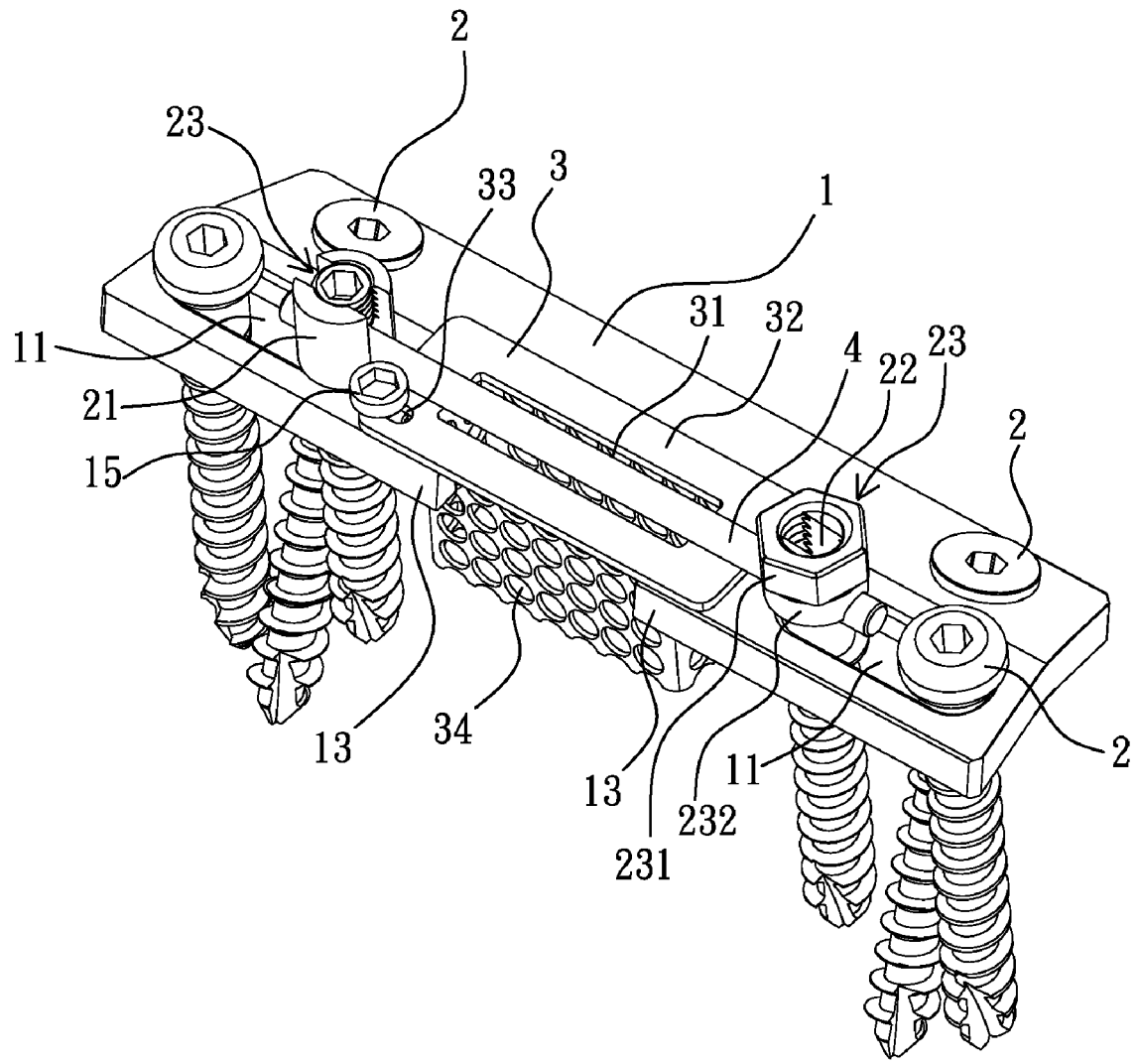
FIG. 4 is an elevational assembly view of the vertebral fixation plate assembly according to the present invention.

As shown in FIG. 4, there are three bone screws 2 on each distal side of the fixation plate 1. The surgeon can decide to install two or three bone screws 2 depend on the patient's bone density status or disease condition, and the head 21 of one bone screw 2 in each of the left-sided elongated holes 11 has a longitudinal crevice 22 for the positioning of the link 4 to reinforce the structural strength of the fixation plate 1. Therefore, the invention has the advantages of a fixation plate as well as the advantages of a fixation rod.

Further, the head 21 of the bone screws 2 in the left-sided elongated holes 11 of the fixation plate 1 can be moved along the respective elongated holes 11 to adjust the fixation position before fastening to the vertebrae. Therefore, this arrangement allows adjustment of the gap between the two vertebrae to which the fixation plate 1 is to be affixed.

The cage 3 is a hollow container, having a cage body 31 inserted through the opening 12 of the fixation plate 1, a top rim 32 extending around the periphery of the top side of the cage body 31 and supported on the fixation plate 1 around the opening 12, a hole 33 on the top rim 32 corresponding to the mounting screw hole 14 on one protrusion 13 of the fixation plate 1. The tie screw 15 is inserted through the hole 33 and threaded into the mounting screw hole 14 to affix the cage 3 to the fixation plate 1. The latticed cage body 31 is for receiving autograft bone, bone allograft, or biomedical bone substitute to enhance the support power. Further, the cage body 31 has a plurality of bone fusion holes 34 distributed through the periphery for bone fusion and growth and for fusion with the vertebral spacer set between the two vertebrae. The cage 3 can be trimmed subject to the desired length so that the cage 3 can be abutted against the vertebral spacer for quick fusion of the autograft bone, bone allograft or biomedical bone substitute in the cage 3 with the autograft bone, bone allograft or biomedical bone substitute in vertebral spacer. The design of the present invention enables the cage 3 to be inserted into the resection site between the two vertebrae and abutted against the vertebral spacer during the surgical operation, facilitating bone fusion.

The link 4 is a round rod attached to the heads 21 of the bone screws 2 that are disposed adjacent to the opening 12 of the fixation plate 1 at two sides, thereby imparting a downward pressure to the top rim 32 against the top wall of the fixation plate 1. Therefore, the link 4 reinforces the strength of the fixation plate 1, holds down the cage 3, and allows adjustment of the bone screws 2 to fit the vertebral column.

Figure 5:
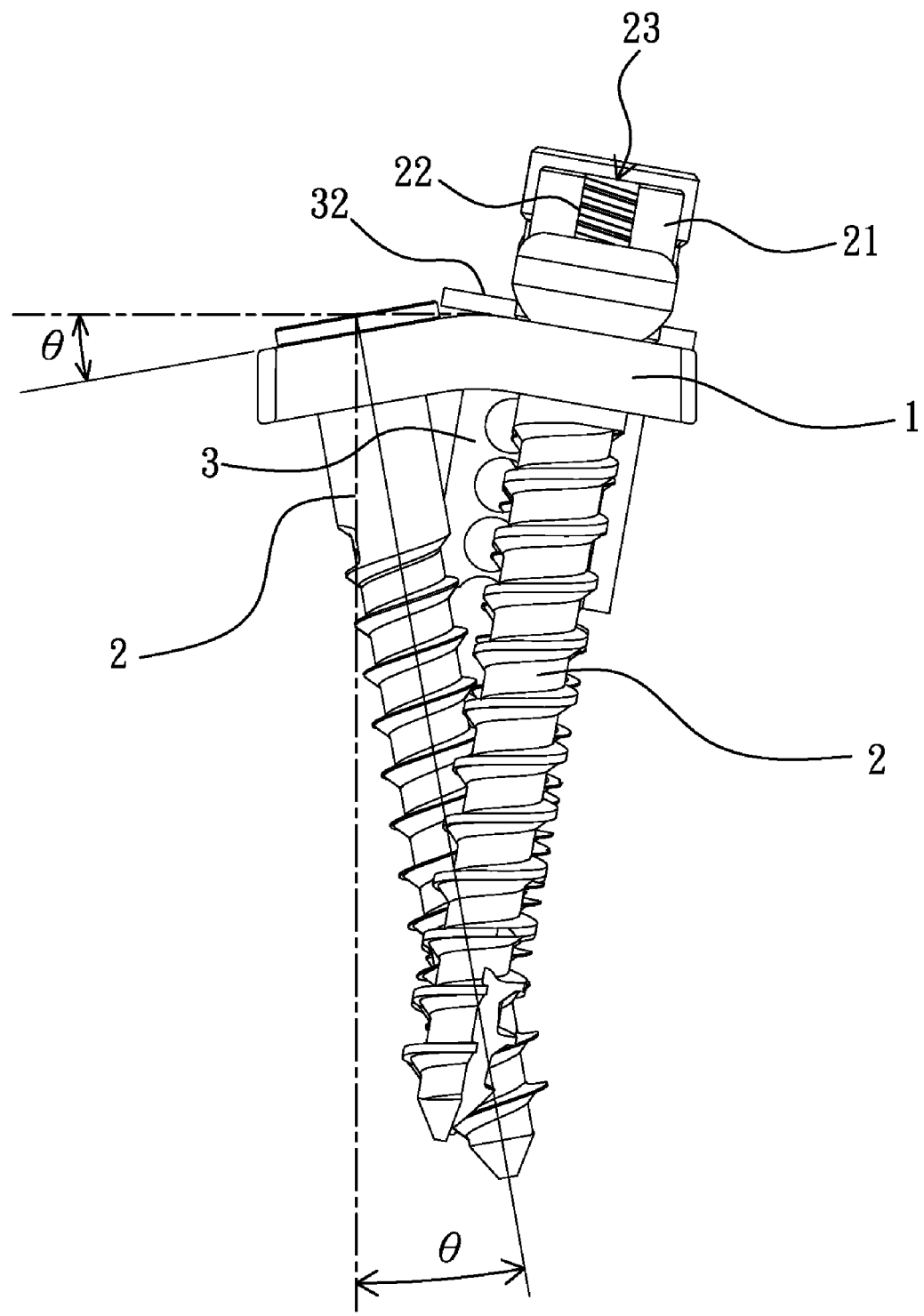
FIG. 5 is a schematic end view of the present invention, showing the vertebral fixation plate assembly assembled.

Referring to FIGS. 4 and 5, when assembled, the cage 3 is affixed to the middle part of the left side of the fixation plate 1, and the link 4 is connected between two bone screws 2 and pressed on the top side of the cage 3. Therefore, the vertebral fixation plate assembly of the present invention provides a bon fusion function similar to a conventional vertebral fusion cage.

Figure 6:
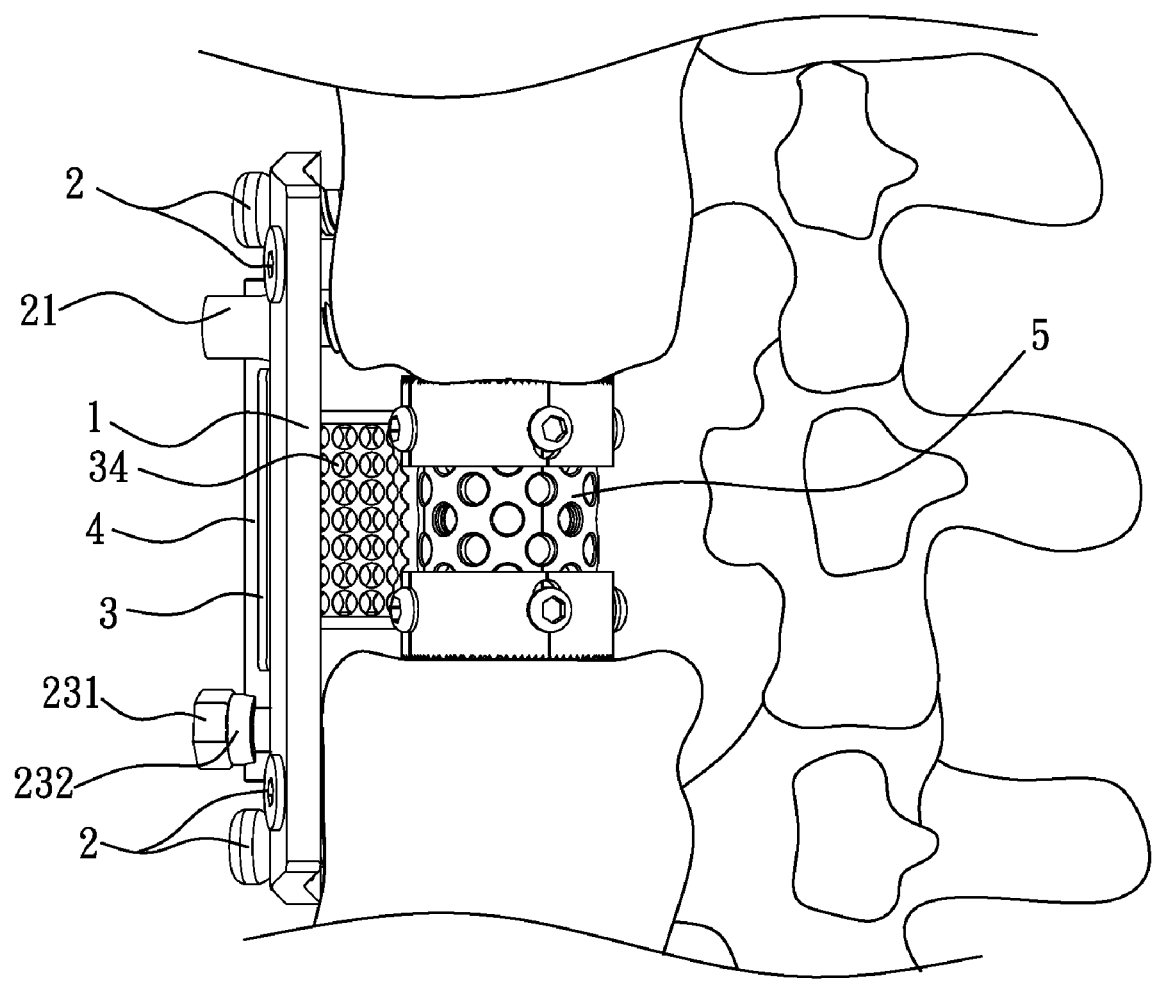
FIG. 6 is a schematic applied view of the present invention showing the vertebral fixation plate assembly affixed to two vertebrae.

FIG. 6 is a schematic drawing showing an application example of the present invention. According to this application example, the third vertebral body of the patients lumbar vertebrae and the intervertebral discs between the second and third lumbar vertebrae and third and fourth lumbar vertebrae are removed from the vertebral column, a vertebral spacer 5 is inserted into the resection site, and the vertebral fixation plate assembly of the present invention is affixed to the two adjacent vertebral bodies above and below the resection site. During the surgical operation, the first lower left bone screw 2 is affixed to the lower fourth vertebral body, and then the fixation plate 1 is attached to the vertebral column, and then the upper right bone screw 2, the first upper left bone screw 2 and the second upper left screw 2 are affixed to the upper second vertebral body. Thereafter, the cage 3 is inserted into the opening 12 of the fixation plate 1, and then autograft bone, bone allograft or biomedical bone substitute is filled in the cage body 31 of the cage 3. Thereafter, the link 4 is inserted into the longitudinal crevices 22 of the heads 21 of the second left upper bone screw 2 and first left lower bone screw 2 to force the second vertebral body and the fourth vertebral body against the vertebral spacer 5 and to simultaneously hold down the cage 3, and then the holding down devices 23 are respectively fastened to the heads 21 of the bone screws 2. Thereafter, the lower right bone screw 2 and the second lower left bone screw 2 are affixed to the fourth vertebral body, and therefore the vertebral fixation plate assembly is fixedly secured to the vertebral bodies above and below the resection site, finishing the vertebral replacement When compared to conventional designs, the invention has a cage set in a middle part of the fixation plate to carry autograft bone, bone allograft or biomedical bone substitute, and uses a longitudinal link to hold down the cage. After implantation, the cage is connected to the implanted vertebral body, improving bone fusion efficiency. The link is an optional member. The surgeon can decide to install or not to install the link subject to the patient's bone density status or disease condition. Therefore, the vertebral fixation plate assembly prevents vertebral sinking or slipping of the vertebral spacer, and reinforces the strength and stiffness of the vertebral column. Further, the cage effectively holds autograft bone, bone allograft or biomedical bone substitute in place, facilitating bone fusion.

Although a particular embodiment of the invention has been described in detail for purposes of illustration, various modifications and enhancements may be made without departing from the spirit and scope of the invention.

What is claimed is:

1. A vertebral fixation plate assembly for insertion into the resection site between two vertebrae of a patient's vertebral column and fixation to front or lateral side of the two adjacent vertebral bodies above and below the resection site, the vertebral fixation plate assembly comprising:
a fixation plate, said fixation plate having an opening on a middle part thereof and a plurality of holes at two distal ends thereof;
a plurality of bone screws inserted through the holes of said fixation plate for affixing said fixation plate to a patient's vertebral column;
a cage, said cage having a cage body mounted in said opening of said fixation plate, said cage body having a plurality of fusion holes cut through the periphery thereof for bone fusion and growth; and
a link connected between two said bone screws at two sides of said opening of said fixation plate to hold down said cage;
wherein each said bone screw to which said link is connected has a longitudinal crevice in a head thereof for receiving one end of said link, and holding down means fastened to the head to hold down the corresponding end of said link.

2. The vertebral fixation plate assembly as claimed in claim 1, wherein said fixation plate has a symmetrically arched cross section, and each sloping top wall of a ridge roof thereof defines with the horizontal reference line at the ridge thereof a contained angle within 40-degrees.

3. The vertebral fixation plate assembly as claimed in claim 1, wherein the holes of said fixation plate include two elongated holes respectively disposed on two distal ends of a left part thereof and two round holes respectively disposed on two distal ends of a right part thereof.

4. The vertebral fixation plate assembly as claimed in claim 1, wherein said fixation plate comprises two protrusions suspending in an outer open side of said opening and aimed at each other for stopping said cage in said opening, and a mounting hole on one said protrusion for the mounting of a tie screw to affix said cage to said fixation plate; said cage comprises a top rim extending around a top side of said cage body and supported on said protrusions, and a hole cut through said top rim and fastened to said mounting hole with a fastening member.

5. The vertebral fixation plate assembly as claimed in claim 1, wherein said holding down means comprises a holding down ring sleeved onto the head of the respective bone screw and attached to the periphery of the corresponding end of said link, and a nut threaded onto the head of the respective bone screw to lock said holding down ring.

6. The vertebral fixation plate assembly as claimed in claim 1, wherein said cage body of said cage is filled with autograft bone, bone allograft or biomedical bone substitute, and is trimmed subject to a predetermined length for abutting against a vertebral spacer that is set in the resection site between the two vertebrae.

7. A vertebral fixation plate assembly for insertion into the resection site between two vertebrae of a patient's vertebral column and fixation to front or lateral side of the two adjacent vertebral bodies above and below the resection site, the vertebral fixation plate assembly comprising:
a fixation plate, said fixation plate having an opening on a middle part thereof and a plurality of holes at two distal ends thereof;
a plurality of bone screws inserted through the holes of said fixation plate for affixing said fixation plate to a patient's vertebral column;
a cage, said cage having a cage body mounted in said opening of said fixation plate, said cage body having a plurality of fusion holes cut through the periphery thereof for bone fusion and growth; and
a link connected between two said bone screws at two sides of said opening of said fixation plate to hold down said cage;
wherein each said bone screw to which said link is connected has a longitudinal crevice in an internally threaded barrel-like head thereof that receives one end of said link, and holding down means fastened to the head to hold down the respective end of said link.

8. The vertebral fixation plate assembly as claimed in claim 7, wherein said holding down means comprises a holding down screw threaded into the internally threaded barrel-like head of the respective bone screw and stopped against the periphery of the corresponding end of said link.

9. The vertebral fixation plate assembly as claimed in claim 7, wherein said fixation plate has a symmetrically arched cross section, and each sloping top wall of a ridge roof thereof defines with the horizontal reference line at the ridge thereof a contained angle within 40-degrees.

10. The vertebral fixation plate assembly as claimed in claim 7, wherein the holes of said fixation plate include two elongated holes respectively disposed on two distal ends of a left part thereof and two round holes respectively disposed on two distal ends of a right part thereof.

11. The vertebral fixation plate assembly as claimed in claim 7, wherein said fixation plate comprises two protrusions suspending in an outer open side of said opening and aimed at each other for stopping said cage in said opening, and a mounting hole on one said protrusion for the mounting of a tie screw to affix said cage to said fixation plate; said cage comprises a top rim extending around a top side of said cage body and supported on said protrusions, and a hole cut through said top rim and fastened to said mounting hole with a fastening member.

12. The vertebral fixation plate assembly as claimed in claim 7, wherein said cage body of said cage is filled with autograft bone, bone allograft or biomedical bone substitute, and is trimmed subject to a predetermined length for abutting against a vertebral spacer that is set in the resection site between the two vertebrae.

13. A vertebral fixation plate assembly for insertion into the resection site between two vertebrae of a patient's vertebral column and fixation to front or lateral side of the two adjacent vertebral bodies above and below the resection site, the vertebral fixation plate assembly comprising:
a fixation plate, said fixation plate having an opening on a middle part thereof and a plurality of holes at two distal ends thereof;
a plurality of bone screws inserted through the holes of said fixation plate for affixing said fixation plate to a patient's vertebral column;
a cage, said cage having a cage body mounted in said opening of said fixation plate, said cage body having a plurality of fusion holes cut through the periphery thereof for bone fusion and growth; and
a link connected between two said bone screws at two sides of said opening of said fixation plate to hold down said cage;
wherein one said bone screw to which said link is connected has a longitudinal crevice in a head thereof for receiving one end of said link and a first holding down means fastened to the head to hold down the corresponding end of said link; the other said bone screw to which said link is connected has a longitudinal crevice in an internally threaded barrel-like head thereof for receiving an opposite end of said link and a second holding down means fastened to the head to hold down the corresponding end of said link.

14. The vertebral fixation plate assembly as claimed in claim 13, wherein said first holding down means comprises a holding down ring sleeved onto the head of the respective bone screw and attached to the periphery of the corresponding end of said link, and a nut threaded onto the head of the respective bone screw to lock said holding down ring; said second holding down means comprises a holding down screw threaded into the internally threaded barrel-like head of the respective bone screw and stopped against the periphery of the corresponding end of said link.

15. The vertebral fixation plate assembly as claimed in claim 13, wherein said fixation plate has a symmetrically arched cross section, and each sloping top wall of a ridge roof thereof defines with the horizontal reference line at the ridge thereof a contained angle within 40-degrees.

16. The vertebral fixation plate assembly as claimed in claim 13, wherein the holes of said fixation plate include two elongated holes respectively disposed on two distal ends of a left part thereof and two round holes respectively disposed on two distal ends of a right part thereof.

17. The vertebral fixation plate assembly as claimed in claim 13, wherein said fixation plate comprises two protrusions suspending in an outer open side of said opening and aimed at each other for stopping said cage in said opening, and a mounting hole on one said protrusion for the mounting of a tie screw to affix said cage to said fixation plate; said cage comprises a top rim extending around a top side of said cage body and supported on said protrusions, and a hole cut through said top rim and fastened to said mounting hole with a fastening member.

18. The vertebral fixation plate assembly as claimed in claim 13, wherein said cage body of said cage is filled with autograft bone, bone allograft or biomedical bone substitute, and is trimmed subject to a predetermined length for abutting against a vertebral spacer that is set in the resection site between the two vertebrae.

* * * * *